(12) United States Patent
Borody

(10) Patent No.: US 6,645,530 B1
(45) Date of Patent: *Nov. 11, 2003

(54) TREATMENT OF GASTRO-INTESTINAL DISORDERS

(75) Inventor: Thomas Julius Borody, Five Dock (AU)

(73) Assignee: Gastro Services Pty Limited, Five Dock (AU)

(*) Notice: Subject to any disclaimer, the term of this patent is extended or adjusted under 35 U.S.C. 154(b) by 0 days.

This patent is subject to a terminal disclaimer.

(21) Appl. No.: 08/474,796

(22) Filed: Jun. 7, 1995

Related U.S. Application Data

(63) Continuation of application No. 08/103,176, filed on Aug. 6, 1993, now Pat. No. 5,443,826, which is a continuation of application No. 06/646,784, filed on Jan. 24, 1991.

(30) Foreign Application Priority Data

| Aug. 2, 1988 | (AU) | ................................. PI9613 |
| Apr. 21, 1989 | (AU) | ................................. PI3837 |
| Aug. 2, 1989 | (WO) | ................ PCT/AU89/00328 |

(51) Int. Cl.[7] ............................... A61K 35/24
(52) U.S. Cl. ................... 424/543; 424/93.3; 424/93.48; 426/61; 426/71
(58) Field of Search ............... 424/543, 93.3, 424/93.48; 426/61, 71, 2

(56) References Cited

U.S. PATENT DOCUMENTS

| 3,713,836 A | 1/1973 | Carlsson ..................... 426/61 |
| 4,335,107 A | 6/1982 | Snoeyenbos ................. 426/61 |
| 4,657,762 A | 4/1987 | Mikkola et al. ............... 426/61 |

FOREIGN PATENT DOCUMENTS

| AU | 53298/79 | 7/1980 |
| AU | 37580/85 | 9/1985 |
| DE | 2134179 | 1/1973 |
| FR | 1275 M | 5/1962 |
| FR | 2427 M | 3/1964 |
| FR | 2828 M | 10/1964 |
| FR | 5528 M | 11/1967 |
| FR | 2244464 | 4/1975 |
| GB | 1271674 | 4/1972 |

OTHER PUBLICATIONS

Bowden, T.A., et al, Am. Surgeon 47 (4):178–183 (1981), BA 72:46142 Abstract.
Zoppi, G., et al, Eur. J. Pediatr. 139(1), 18–21 (1982) Abstract BA 75:78280.
Schwan et al, The Lancet, 845, Oct. 8, 1983.
Tvede, M., et al, The Lancet, 1156–1160, May 27, 1989.
Eiseman, B., et al, Surgery 44: 854–859 (1958).
Zoppi, G., et al, Eur. J. Pediatr. 139, 22–24 (1982)—Full article and BA 75:78281 Abstract.

Primary Examiner—Jean C. Witz

(57) ABSTRACT

A method of treating chronic disorders associated with the presence of abnormal microflora or an abnormal distribution of microflora in the gastrointestinal tract involves removing the host's existing enteric microflora and substitution of feces from a disease screener donor or composition comprising microorganism selected from the group consisting of Bacteroides and *E. coli*.

30 Claims, No Drawings

TREATMENT OF GASTRO-INTESTINAL DISORDERS

This is a continuation of application Ser. No. 08/103,176, filed Aug. 6, 1993, now U.S. Pat. No. 5,443,826, which is a continuation of Ser. No. 06/646,784, filed on Jan. 24, 1991.

TECHNICAL FIELD

The present invention relates to methods of treating diseases in mammals, in particular to the treatment of chronic disorders associated with the presence of abnormal or an abnormal distribution of microflora in the gastrointestinal tract. The invention also relates to pharmaceutical compositions suitable for the treatment of such disorders.

BACKGROUND ART

There are large numbers of patients suffering from gastrointestinal symptoms referrable to the lower small bowel and large bowel which to date have eluded explanation. These disorders include irritable bowel syndrome (IBS) or spastic colon, idiopathic ulcerative colitis, mucous colitis, collagenous colitis, Crohn's disease, inflammatory bowel disease in general, microscopic colitis, antibiotic-associated colitis, idiopathic or simple constipation, diverticular disease, and AIDS enteropathy. Pathophysiology of these disorders eludes logical explanation in spite of decades of research and millions of dollars of research funds. A common underlying factor shared by all these disorders observed by the present inventor is their onset following some extraneous invading infection. In all the disorders, the infection cannot be demonstrated due to our inability to detect infecting agents whose cultural characteristics are unknown to medical science.

Circumstantial evidence which suggests that these disorders are "infection-related" includes:

(a) onset following a gastro-intestinal infection which failed to completely resolve;

(b) transient improvement with use of certain antibiotics, but recurrence upon cessation of antibiotics;

(c) transient improvement following orthostatic lavage prior to colonoscopy and;

(d) transient symptom improvement with use of "colonic" irrigation

It is impractical to use long-term antibiotic therapy (with its associated complications) in such patients since cure is not obtained with its use. Furthermore, chronic gut infections with recognised, specific pathogens such as *Clostridium difficile, Yersinia enterocolitica* or *Campylobacter jejuni/coli* are not eradicated with antibiotics. Some previous attempts have been made to alter the enteric microflora in order to eradicate such chronic infections. These measures nevertheless indicate that alteration of bacterial flora may effect dramatic clinical improvement in conditions characterized by chronic, resistant enterocolitic infection. However there remain many chronic disorders of uncertain aetiology or causation, which are resistant to cure by current therapeutic techniques.

OBJECTS OF THE INVENTION

It is thus an object of the present invention to provide novel methods of treating various disease states related to the presence of "abnormal" microflora in the gastrointestinal tract.

DISCLOSURE OF THE INVENTION

The present invention recognises chronic infection/infestation as the underlying pathological process in a wide range of chronic disorders such as irritable bowel syndrome, particularly when characterised by chronic abdominal pain, bloating, or excessive flatulence, together with chronic diarrhoea or alternating constipation/diarrhoea, and also in spastic colon, mucous colitis, collagenous colitis, ulcerative colitis, Crohn's colitis, microscopic colitis, idiopathic inflammatory bowel disease, antibiotic-associated colitis, idiopathic or simple constipation, diverticular disease and AIDS enteropathy.

The invention has also been found to relate to other gastrointestinal disorders of unexplained aetiology such as polyposis coli and colonic polyps, which may well be influenced by the local bowel microflora.

In addition the present invention also provides a method of treatment of chronic gastrointestinal infections with specific microorganisms such as *Clostridium difficile*, Yersinia spp, Campylobacter spp, Aeromonas spp, *E. coli*, Cryptosporidium spp, Amoebae, Giardia and even chronic viral infections, and of small bowel bacterial overgrowth.

The present invention furthermore, recognises the close association between the intestine and liver disease, and the intestine and migraines and chronic fatigue syndrome, and possibly other neurological syndromes such as, multiple sclerosis, amyotrophic lateral sclerosis, myasthenia gravis, Parkinson's disease, Alzheimers disease and other degenerative disorders. Hence, it is proposed that a considerable proportion of currently unexplained diseases of the liver and nervous system of unknown aetiology may be explicable by the chronic storage of pathogens within the small/large intestine and the subsequent passage of antigenic material and pathogenic TOXINS into the portal system (liver damage) or systemic circulation (neurological conditions). Specifically, such hepato/biliary system disorders as primary biliary cirrhosis, primary sclerosing cholangitis, fatty liver of unknown aetiology, or cryptogenic cirrhosis, may be secondary to chronic pathogen carrier state in the intestine.

The links between the intestine and joint disease are also recognised. Joint diseases such as rheumatoid arthritis, the non-rheumatoid arthritidies including, ankylosing spondylitis, and Reiter's syndrome, may also be causally related to a chronic intestinal carrier state, as may other syndromes with an immune mediated component such as glomerulonephritis, haemolytic uraemic syndrome, juvenile diabetes mellitus, Behcet's syndrome, coeliac disease and dermatitis herpetiformis. Similarly, syndromes with an immune complex mediated component, such as scleroderma, systemic lupus erythematosus, mixed cryoglobulinaemia, polyarteritis, familial Mediterranean fever, amyloidosis, and the various presentations of such syndromes, together with such "idiopathic" states as chronic urticaria, may be manifestations of variations of immune regulated responses to related bowel-origin pathogens chronically shedding their antigen(s) into the circulation. Other chronic conditions such as acne, and chronic idiopathic pseudo-obstructive syndrome, may well be influenced by similar mechanisms.

For many of these syndromes present therapy offers only palliation of symptoms and/or the induction of remission of the disease process but not cure. The present inventor therefore recognised the need to find a curative therapy for these wide ranging disease processes associated with considerable morbidity.

Thus according to a first embodiment of the invention there is provided a method of treatment or prophylaxis of a chronic disorder associated with the presence in the gastrointestinal tract of a host of abnormal or an abnormal distribution of microflora for said host, which method comprises the removal of at least a portion of the host's existing enteric microflora and the substitution of an effective amount of predetermined microflora.

In its preferred form the treatment should effect a cure of the symptoms of such disorders. The change of flora is preferably as "near-complete" as possible and the flora is replaced by viable organisms which will crowd out any remaining, original flora.

The method of the present invention is applicable to animals in general in particular humans and economically significant domestic animals.

In the case of humans, the present invention encompasses methods of treatment of chronic disorders associated with the presence of abnormal enteric microflora. Such disorders include but are not limited to those conditions in the following categories:

i) gastro-intestinal disorders including irritable bowel syndrome or spastic colon, ulcerative colitis, mucous colitis, collagenous colitis, Crohn's disease, inflammatory bowel disease, microscopic colitis, antibiotic associated colitis, idiopathic or simple constipation, diverticular disease, AIDS enteropathy, small bowel bacterial overgrowth, coeliac disease, polyposis coli, colonic polyps, chronic idiopathic pseudo obstructive syndrome;

ii) chronic gut infections with specific pathogens including bacteria, viruses, fungi and protozoa;

iii) liver disorders such as primary biliary cirrhosis, primary sclerosing cholangitis, fatty liver or cryptogenic cirrhosis;

iv) joint disorders such as rheumatoid arthritis, non-rheumatoid arthritidies, ankylosing spondylitis, and Reiter's syndrome;

v) immune mediated disorders such as glomerulonephritis, haemolytic uraemic syndrome, juvenile diabetes mellitus, mixed cryoglobulinaemia, polyarteritis, familial Mediterranean fever, amyloidosis, scleroderma, systemic lupus erythematosus, and Behcet's syndrome;

vi) neurological syndromes such as migraine, multiple sclerosis, amyotrophic lateral sclerosis, myasthenia gravis, chronic fatigue syndrome, Parkinson's disease, Alzheimers disease and other degenerative disorders;

vii) dermatological conditions such as, chronic urticaria, acne, dermatitis herpetiformis and vasculitic disorders;

The above disorders are all characterised by their response to treatment with the method of the present invention.

Typically the change in enteric flora comprises:

(a) substantially complete removal of existing enteric flora, and (b) introduction of an array of predetermined flora into the gastro-intestinal system, and thus in a preferred form the method of treatment comprises substantially completely changing enteric flora in patients requiring such treatment.

Furthermore, in some of these disorders a short course of antibiotics may be required to rid tissue-invasive pathogens originating in the bowel lumen. For example, in Crohn's disease, anti-tuberculosis therapy may be required for six to twelve weeks before the bowel is cleared out and the flora content exchanged for a predetermined flora.

Preferably the removal of existing enteric flora is effected a lavage of the gastro-intestinal tract. This can be effected by methods known to those skilled in the art such as ingestion of lavage solutions such as orthostatic salt and polyethylene glycol solution, enemas or small bowel intubation and lavage.

Turning to the introduction of an array of predetermined flora into the gastro-intestinal system, this can be effected by enemas or per-colonoscope, via intubation of the small bowel using for example a large bore catheter equipped with distal balloon to effect rapid passage down the jejunum, or via the oral route with enteric-coated capsules.

The predetermined array of normal bowel microflora preferably comprises a composition of fresh homologous faeces, equivalent freeze-dried and reconstituted faeces or a "synthetic" faecal composition.

In a preferred form the synthetic faecal composition comprises a preparation of viable flora which preferably in proportional content, resembles normal healthy human faecal flora. Suitable microorganisms may be selected from the following; Bacteroides, Bifidobacterium, Eubacteria, Fusobacteria, Propionibacteria, Lactobacilli, anaerobic cocci Ruminococcus, E. coli, Gemmiger, Clostridium, Desulfomonas, species and, more specifically, bacteria selected from Table 1. Preferably fungi are also present such as Monilia.

According to a second embodiment of the invention there is provided a pharmaceutical composition useful for the treatment and/or prophylaxis of chronic disorders associated with the presence in the gastro-intestinal tract of a host of abnormal or an abnormal distribution of microflora for said host, which composition comprises a selection of viable microorganisms in appropriate proportions such that the composition substantially resembles the host's normal healthy, faecal flora.

In practice suitable microorganisms include those selected from Bacteroides, Bifidobacterium, Eubacteria, Fusobacteria, Propionibacteria, Lactobacilli, anaerobic cocci, Ruminococcus, E. coli, Gemmiger, Clostridium, Desulfomonas, and Monilia species, and more specifical from those set out in Table 1.

In a preferred form the composition comprises a liquid culture of Bacteroides and E. coli.

The pharmaceutical composition of the present invention is preferably lyophilised, pulverised and powdered. It may then be infused, dissolved such as in saline, as an enema. Alternatively the powder may be encapsulated as enteric-coated capsules for oral administration. As a powder it can preferably be provided in a palatable form for reconstitution for drinking. The composition can be combined with other adjuvants such as antacids to dampen bacterial inactivation in the stomach. Acid secretion in the stomach could also be pharmacologically suppressed using H2-antagonists or omeprazole. The powder may be reconstituted also to be infused via naso-duodenal infusion.

The present composition is therefore preferably in the form of:

i) an enema composition which can be reconstituted with an appropriate diluent;

ii) enteric-coated capsules, or iii) powder for reconstitution with an appropriate diluent for naso-enteric infusion or colonoscopic infusion, or iv) powder for reconstitution with appropriate diluent, flavouring and gastric acid suppression agent for oral ingestion.

Furthermore the present invention also relates to the treatment of animals, in particular to the treatment of gastro-intestinal disorders in eccomically important domestic animals, such as cattle, sheep, horses, pigs, goats etc. The method of the present invention has been found to be especially useful in the treatment of the various forms of necrotising enterocolitis which can be a major problem in animal stocks.

Obviously in the treatment of animals the appropriate composition of microflora will vary according to the species being treated and the constituent normal flora known to inhabit the gut. Thus the composition according to the invention would comprise, a preparation of viable flora which preferably in proportional content, resembles the normal healthy faecal flora of the species involved. The compositions may be prepared in any of the forms already described and administered accordingly.

BEST METHOD OF PERFORMING THE INVENTION

Typically the method of the invention is applicable to a patient suffering from a chronic disorder associated with the presence of abnormal microflora in the gastro-intestinal tract such as irritable bowel syndrome.

In the practice of the invention the patients existing enteric flora is removed by gastro-intestinal lavage effected by ingestion of about 3 liters of a balanced salt solution with polyethylene glycol. Lavage is continued until the removal of the existing flora is as near complete as possible.

A composition of predetermined flora in the form of a liquid culture of Bacteroides and *E. coli* is then infused into the patient per colonoscope in an amount sufficient to replace the removed flora, and reverse the disease process. Alternatively fresh homologous faeces obtained from a disease screened donor are liquefied and mixed with unprocessed bran. The mixture is then homogenised anaerobically under $CO_2$ cover and infused into the patient per colonoscope.

Cure or remission of symptoms is then monitored subjectively and by assessment of stool frequency or other appropriate criteria.

Using liquid cultures of Bacteroides and *E. coli* the inventor has achieved total reversal of colitis, irritable bowel syndrome and constipation.

As indicated in the method of treatment aspect of the invention, a preparatory course of appropriate antibiotics may be used. For example. Septrin for chronic yersiniasis, Metronidazole for ulcerative colitis, anti-TB therapy in Crohn's disease, or Vancomycin in chronic *Clostridium difficile* infestations.

TABLE 1

| % of flora[b] | Organism(s) |
| --- | --- |
| 11.8(0.90) | *Bacteroides fragilis* ss. *vulgatus* |
| 9.9(0.83) | *Eubacterium aerofaciens* |
| 8.9(0.78) | *Bacteroides fragilis* ss. *thetaiotaomicron* |
| 6.6(0.68) | *Peptostreptococcus productus* II |
| 6.0(0.64) | *Bacteroides fragillis* ss. *distasonis* |
| 4.4(0.55) | *Fusobacterium prausnitzii* |
| 3.5(0.49) | *Coprococcus eutactus* |
| 3.0(0.45) | *Eubacterium aerofaciens* III |
| 2.8(0.44) | *Peptostreptococcus productus* I |
| 2.7(0.43) | *Ruminococcus bromii* |
| 2.6(0.43) | *Bifidobacterium adolescentis* |
| 2.2(0.39) | *Gemmiger formicilis, Bifidobacterium longum* |
| 2.1(0.38) | *Eubacterium siraeum* |
| 1.8(0.35) | *Ruminococcus torques* |
| 1.7(0.34) | *Eubacterium rectale* III-H |
| 1.6(0.33) | *Eubacterium rectale* IV, *Eubacterium eligens* |
| 1.5(0.32) | *Bacteroides eggerthii* |

TABLE 1-continued

| % of flora[b] | Organism(s) |
| --- | --- |
| 1.4(0.31) | *Clostridium leptum* |
| 1.3(0.29) | *Bacteroides fragilis* ss. a |
| 1.2(0.29) | *Eubacterium biforme* |
| 0.91(0.25) | *Bifidobacterium infantis* |
| 0.84(0.24) | *Eubacterium rectale* III-F |
| 0.57(0.20) | *Coprococcus comes, Bacteroides capillosus* |
| 0.50(0.18) | *Ruminococcus albus, Eubacterium formicigenerans, Eubacterium hallii, Eubacterium ventriosum* I, *Fusobacterium russii* |
| 0.43(0.17) | *Ruminococcus obeum, Eubacterium rectale* II, *Clostridium ramosum* I, *Lactobacillus leichmanii* |
| 0.35(0.16) | *Ruminococcus callidus, Butyrvibrio crossotus* |
| 0.30(0.14) | *Acidaminococcus fermentans, Eubacterium ventriosum, Bacteroides fragilis* ss. *fragilis*, Bacteroides AR |
| 0.23(0.12) | *Coprococcus catus, Eubacterium hadrum, E. cylindroides, E. ruminantium,* Eubacterium CH-1 , *Staphylococcus epidermidis* |
| 0.17(0.10) | *Peptostreptococcus* BL, *Eubacterium limosum, Bacteroides praeacutus,* Bacteroides L, *Fusobacterium mortiferum* I, *F. naviforme, Clostridium innocuum, C. ramosum, Propionibacterium acnes, Ruminococcus flavefaciens* |
| 0.10(0.08) | *Ruminococcus* AT, *Peptococcus* AU-1, Eubacterium AG, -AK, -AL, -AL-1, -AN; *Bacteroides fragilis* ss. *ovatus*, -ss. d, -ss. f; Bacteroides L-1, L-5; *Fusobacterium nucleatum, F. mortiferum, Esherichia coli, Streptococcus morbillorum* |
| 0.05(0.05) | *Peptococcus magnus,* Peptococcus G, -AU-2; *Streptococcus intermedius, Ruminococcus lactaris,* Ruminococcus CO, Gemmiger X, Coprococcus BH, -CC; *Eubacterium tenue, Eubacterium ramulus,* Eubacterium AE, -AG-H, -AG-M, -AJ, -BW-1; *Bacteroides clostridiiformis* ss. *clostridiiformis, B. coagulans, B. oralis, B. ruminicola* ss. *brevis,* -ss. *ruminicola, Bacteroides splanchnicus, Desulfomonas pigra,* Bacteroides L-4, -W-1; Fusobacterium H, Lactobacillus G, Succinivibrio A |

[b]The percentage of the fecal population (the standard deviation of the estimate is given in parentheses).

The invention will now be further described with reference to the following non-limiting examples.

EXAMPLE 1

A 28 year old male presented with bloody diarrhoea, 7 to 12 times per day, weight loss, anaemia, arthritis, marked liver-function blood test abnormalities, colonoscopic findings of "pancolitis" and histologic diagnosis of active chronic colitis. Following two years of "standard" anti-colitis therapy he improved markedly. The anaemia was corrected, he gained weight and his liver functions improved somewhat. However, he continued to experience three to four stools per day in spite of 9×500 mg salazopyrin tablets per day and second-nightly steriod enemas (Predsol Enemas). Furthermore, liver function tests remained elevated. Following one week of metronidazole tablets 200 mg×4 per day, and oral ingestion of three liters balanced salt solution with polyethylene glycol (GLYCOPREP), he received fresh, liquefied homogenized human donor faeces from a disease-screened donor were infused into the patient. Prior to infusion unprocessed bran was added to the faeces and homogenization was carried out anaerobically under $CO_2$ cover.

Following infusion, the patient has remained well and off all treatment for three months to date. Liver function tests have returned to normal. He has one formed stool per day and has begun to put on weight. He has no arthralgia.

EXAMPLE 2

Similar methods were used to treat 55 patients suffering with either constipation, diarrhoea, abdominal pain, ulcerative colitis or Crohn's disease. Patients were treated when other forms of therapy had failed to control their symptoms. Following bowel flora alteration 20 patients were deemed "cured", 9 improved, while 26 failed to improve. The following cases illustrate "cures" using the method of the invention over a follow up period of 1 to 12 months.

Case 1 Chronic Constipation

A 31 year old female who had a history of chronic constipation commencing at birth with a frequency of once per week without laxatives. Following bowel flora alteration she has had daily or second stool frequency, without resort to laxatives and remains well at six month follow-up.

Case 2 Chronic Pain-Predominant IES

This 21 year old female was thoroughly investigated over a four year period for severe colickly abdominal pain, requiring frequent admissions and narcotic pain relief. Multiple investigations included endoscopy, laparoscopy and laparotomy. Five days following alteration of her bowel flora she was pain free and remains pain free at four months follow-up.

Case 3 Chronic Diarrhoea-Predominant IBS

A 35 year old female presented with a history of several years of diarrhoea (2–10/d) and associated abdominal pain. Her only abnormal investigation was +ve stool latex test for clostridium difficile toxin. This failed to clear after a course of Vancomycin and she underwent bowel flora alteration with resolution of her chronic diarrhoea. Diarrhoea and pain have not recurred at one month follow-up.

Case 4 Chronic Ulcerative Colitis

This 45 year old man presented with an 18 month history of ulcerative colitis and elevated liver transaminases. Pancolitis was confirmed on colonoscopy. Sulfasalazine caused a rash while olsalazine gave inadequate relief. The patient underwent exchange of bowel flora improving adequately enough to come off treatment within days. At three months he continues to feel well, has no diarrhoea and is on no medication. His liver transaminases have returned to normal. Colonoscopy is now normal and mucosal biopsies are now normal.

Case 5 Crohn's Disease

This 31 year old man was admitted to hospital with small bowel obstruction subsequently shown on small bowel enema to be Crohn's disease of the terminal ileum. This was confirmed on terminal ileal biopsy. In spite of prednisone and sulfasalazine, hypoproteinaemia with ankle oedema was prominent presumably due to protein losing enteropathy. Three days following bowel flora alteration his ankle oedema and serum proteins returned to normal. He remains free of symptoms, off therapy 4 months later.

Case 6 Irritable Bowel/chronic Fatigue Syndrome

This 42 year old woman presented with symptoms of irritable bowel syndrome characterised by diarrhoea and pain, and also complained of profound tiredness. Faecal infusion reversed the bowel symptoms. In addition the profound tiredness suddenly disappeared. Similar results were obtained in 4 related cases.

What is claimed is:

1. A method for the treatment of a chronic gastro-intestinal disorder selected from the group consisting of spastic colon, mucous colitis, collagenous colitis, inflammatory bowel disease, microscopic colitis, idiopathic or simple constipation, diverticular disease, chronic idiopathic pseudo obstructive syndrome and chronic enteric infections, in an adult human host, where the causative agent is unknown, which method comprises substantially completely removing the host's existing enteric microflora by a method comprising using a lavage, and the substitution of an effective amount of fresh or dried or reconstituted feces from a disease-screened human donor or the administration of an effective amount of a pharmaceutically acceptable composition comprising microorganism selected from the group consisting of Batcteroides and *E. coli* in liquid culture or dried viable form.

2. The method of claim 1 wherein said composition comprises Bacteroides.

3. The method of claim 1 wherein said composition comprises *E. coli*.

4. The method of claim 1 wherein the composition further comprises at least one microorganism selected from the group consisting of:
   Bifidobacterium, Eubacteria, Fusobacteria, Propionibacteria, Lactobacilli, anaerobic cocci, Ruminococcus, Gemmiger, Clostridium, Desulfomonas, Monilia species, and mixtures thereof.

5. The method of claim 1 wherein the removal of existing enteric microflora is carried out by gastro-intestinal lavage with orthostatic salt solution and polyethylene glycol solution.

6. The method of claim 5 wherein gastro-intestinal lavage is effected by enemata, oral ingestion or per enteral infusion.

7. The method of claim 1 wherein the composition is introduced into the patient's gastro-intestinal system by ingestion or by per enteral infusion.

8. The method of claim 1 further comprising the administration of an effective amount of at least one antibiotic prior to the removal of the existing enteric microflora.

9. A method for the treatment of a chronic gastro-intestinal disorder selected from the group consisting of ulcerative colitis, Crohn's disease, and irritable bowel syndrome, in an adult human host, where the causative agent is unknown, which method comprises substantially completely removing the host's existing enteric microflora by a method comprising using a lavage, and the substitution of an effective amount of fresh or dried or reconstituted feces from a disease-screened human donor or the administration of an effective amount of a pharmaceutically acceptable composition comprising microorganism selected from the group consisting of Bacteroides and *E. coli* in liquid culture or dried viable form.

10. The method of claim 9 wherein said composition comprises, Bacteroides.

11. The method of claim 9 wherein said composition comprises *E. coli*.

12. The method of claim 9 wherein the composition further comprises at least one microorganism selected from the group consisting of:
   Bifidobacterium, Eubacteria, Fusobacteria, Propionibacteria, Lactobacilli, anaerobic cocci, Ruminococcus, Gemmiger, Clostridium, Desulfomonas, Monilia species, and mixtures thereof.

13. The method of claim 9 wherein the removal of existing enteric microflora is carried out by gastro-intestinal lavage with orthostatic salt solution and polyethylene glycol solution.

14. The method of claim 13 wherein gastro-intestinal lavage is effected by enemata, oral ingestion or per enteral infusion.

15. The method of claim 9 wherein the composition is introduced into the patient's gastro-intestinal system by ingestion or by per enteral infusion.

16. The method of claim 9 further comprising the administration of an effective amount of at least one antibiotic prior to the removal of the existing enteric microflora.

17. The method of claim 8 wherein said antibiotic is metronidazole.

18. The method of claim 16 wherein said antibiotic is metronidazole.

19. A method for treating a chronic disorder associated with the presence of abnormal enteric microflora in an individual comprising substantially completely removing the existing enteric microflora of the individual by a lavage and the administration in place thereof of an effective amount of fresh or dried or reconstituted feces from a disease screened donor or of a pharmaceutically acceptable composition comprising microorganism selected from the group consisting of Bacteroides and *E. coli* in liquid culture or dried viable form.

20. The method of claim 19 where the lavage is performed with orthostatic salt solution and polyethylene glycol solution.

21. The method of claim 19 where the lavage is effected by enema, oral ingestion or per enteral infusion.

22. The method of claim 19 further comprising the administration of an effective amount of at least one antibiotic prior to the removal of the existing microflora.

23. The method of claim 22 wherein said antibiotic is metronidazole.

24. The method of claim 19 wherein the administration is of a pharmaceutically acceptable composition comprising Bacteroides and *E. coli*.

25. The method of claim 24 where the composition further comprises Clostridium.

26. The method of claim 19 wherein the composition further comprises at least one microorganism selected from the group consisting of Bifidobacterium, Eubacteria, Fusobacteria, Propionibacteria, Lactobacilli, anaerobic cocci, Ruminococcus, Gemmiger, Clostridium, Desulfomonas, Monilia species, and mixtures thereof.

27. The method of claim 19 where the chronic disorder is a chronic gastro-intestinal disorder.

28. A method for treating a chronic gastro-intestinal disorder in an individual comprising substantially completely removing the existing enteric microflora of the individual by a lavage and the administration in place thereof of an effective amount of fresh or dried or reconstituted feces from a disease screened donor or of a pharmaceutically acceptable composition comprising microorganism selected from the group consisting of Bacteroides and *E. coli* in liquid culture or dried viable form.

29. The method of claim 27 wherein the administration is of an effective amount of a pharmaceutically acceptable composition comprising Bacteroides and *E. coli*.

30. The method of claim 29 wherein the composition further comprises Clostridium.

* * * * *